United States Patent
Kirwan et al.

(10) Patent No.: US 11,826,331 B2
(45) Date of Patent: Nov. 28, 2023

(54) CAPRIC ACID AND MYRISTIC ACID COMPOSITIONS FOR TREATING CONDITIONS

(71) Applicant: The Cleveland Clinic Foundation, Cleveland, OH (US)

(72) Inventors: John Kirwan, Fairview Park, OH (US); Suzy Comhair, Concord Township, OH (US); Kewal Asosingh, Eastlake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 643 days.

(21) Appl. No.: 16/345,880

(22) PCT Filed: Oct. 30, 2017

(86) PCT No.: PCT/US2017/059000
§ 371 (c)(1),
(2) Date: Apr. 29, 2019

(87) PCT Pub. No.: WO2018/081694
PCT Pub. Date: May 3, 2018

(65) Prior Publication Data
US 2020/0230094 A1   Jul. 23, 2020

Related U.S. Application Data

(60) Provisional application No. 62/414,942, filed on Oct. 31, 2016.

(51) Int. Cl.
| | | |
|---|---|---|
| *A61K 31/20* | (2006.01) | |
| *A23L 27/00* | (2016.01) | |
| *A23L 33/12* | (2016.01) | |
| *A23L 33/17* | (2016.01) | |
| *A23L 33/125* | (2016.01) | |
| *A23L 33/00* | (2016.01) | |
| *A61P 11/06* | (2006.01) | |
| *A23D 9/00* | (2006.01) | |
| *A61K 9/00* | (2006.01) | |

(52) U.S. Cl.
CPC ............... *A61K 31/20* (2013.01); *A23D 9/00* (2013.01); *A23L 27/00* (2016.08); *A23L 33/12* (2016.08); *A23L 33/125* (2016.08); *A23L 33/17* (2016.08); *A23L 33/40* (2016.08); *A61K 9/0019* (2013.01); *A61K 9/0056* (2013.01); *A61P 11/06* (2018.01); *A23V 2002/00* (2013.01)

(58) Field of Classification Search
CPC ......... A61K 31/20; A23L 33/12; A23L 33/17; A23L 33/125; A23L 33/40
See application file for complete search history.

(56) References Cited

U.S. PATENT DOCUMENTS

| | | | |
|---|---|---|---|
| 2013/0045915 A1 | 2/2013 | Dipietro | |
| 2015/0164840 A1 | 6/2015 | O'Donnell et al. | |

FOREIGN PATENT DOCUMENTS

| | | |
|---|---|---|
| CN | 102065699 | 5/2011 |
| CN | 103608005 | 2/2014 |
| WO | WO99/52508 | 10/1999 |
| WO | WO2004/084829 A2 | 10/2004 |
| WO | WO 2009/072097 | 6/2009 |
| WO | WO 2009/131939 | 10/2009 |
| WO | WO 2012/141575 | 10/2012 |
| WO | WO2013/186570 A1 | 12/2013 |

OTHER PUBLICATIONS

International Search Report and Written Opinion for PCT/US17/59000, dated Jan. 9, 2018. 8 pages.
Extended European Search Report for PCT/US17/59000, dated Mar. 20, 2020. 8 pages.
Liu. Medium-chain triglyceride (MCT) ketogenic therapy. Epilepsia. Nov. 2008;49 Suppl 8:33-6.
Schrauwen et al., Fiber type dependent upregulation of human skeletal muscle UCP2 and UCP3 mRNA expression by high-fat diet. Int J Obes Relat Metab Disord. Apr. 2001;25(4):449-56.
Temme et al., Effects of medium chain fatty acids (MCFA), myristic acid, and oleic acid on serum lipoproteinds in healthy subjects. Journal of Lipid Research, Sep. 1, 1997, pp. 1746-1754.

*Primary Examiner* — James D. Anderson
(74) *Attorney, Agent, or Firm* — Casimir Jones, S.C.; Jason R. Bond

(57) ABSTRACT

Provided herein are compositions, articles of manufacture, food products, and methods for treating certain conditions, such as fibrotic disease (e.g., asthma). For example, in certain embodiments, provided herein are food products (e.g., that are ketogenic) that contain high levels (e.g., at least 10% by weight of the food product) of capric acid (C10), myristic acid (C14), or combination thereof (e.g., as free fatty acids or as triglycerides). In other embodiments, methods are provided for receiving an order for such a food product, and shipping the food product to a subject with fibrotic disease (e.g., after receiving or verifying prescription information). In some embodiments, methods are provided of administering or providing a composition to a subject such that the subject receives at least 50 grams per day (e.g., 200 grams per day), on multiple days, of capric acid (C10), myristic acid (C14), or combination thereof.

19 Claims, 11 Drawing Sheets

CAPRIC ACID AND MYRISTIC ACID COMPOSITIONS FOR TREATING CONDITIONS

CROSS-REFERENCE TO RELATED APPLICATIONS

This application claims priority to U.S. Provisional Application No. 62/414,942, filed Oct. 31, 2016, which is herein incorporated by reference in its entirety.

GOVERNMENT FUNDING

This invention was made with government support under grant number HL103453 awarded by National Institutes of Health. The government has certain rights in the invention.

FIELD

Provided herein are compositions, articles of manufacture, food products, and methods for treating certain conditions, such as fibrotic disease (e.g., asthma). For example, in certain embodiments, provided herein are food products (e.g., that are ketogenic) that contain high levels (e.g., at least 10% by weight of the food product) of capric acid (C10), myristic acid (C14), or combination thereof (e.g., as free fatty acids or as triglycerides). In other embodiments, methods are provided for receiving an order for such a food product, and shipping the food product to a subject with fibrotic disease (e.g., after receiving or verifying prescription information). In some embodiments, methods are provided of administering or providing a composition to a subject such that the subject receives at least 50 grams per day (e.g., 200 grams per day), on multiple days, of capric acid (C10), myristic acid (C14), or combination thereof.

BACKGROUND

Approximately 38 million Americans have been diagnosed with asthma by a health professional during their lifetime. This chronic inflammatory disease places a significant burden on both the health care system and individual patients, with annual expenditures for health and lost productivity due to asthma estimated at over $20 billion. In spite of high morbidity and costs, most asthmatic patients have mild-to-moderate disease and about 5-8% of asthmatic patients fall into the category of "chronic severe asthma" (CSA). Asthmatic patients have significant reduction in quality of life as a result of their asthma, have frequent hospital admissions and emergency visits, and account for a much larger percentage of overall health care costs. Clinically, asthma is characterized by a component of irreversible airflow obstruction and peripheral airways disease, ongoing mediator release and a reduced association with atopy.

SUMMARY

Provided herein are compositions, articles of manufacture, food products, and methods for treating certain conditions, such as fibrotic disease (e.g., asthma). For example, in certain embodiments, provided herein are food products (e.g., that are ketogenic) that contain high levels (e.g., at least 10% by weight of the food product) of capric acid (C10), myristic acid (C14), or combination thereof (e.g., as free fatty acids or as triglycerides). In other embodiments, methods are provided for receiving an order for such a food product, and shipping the food product to a subject with fibrotic disease (e.g., after receiving or verifying prescription information). In some embodiments, methods are provided of administering or providing a composition to a subject such that the subject receives at least 50 grams per day (e.g., 200 grams per day), on multiple days, of capric acid (C10), myristic acid (C14), or combination thereof.

In some embodiments, provided herein are compositions and/or articles of manufacture comprising a food product, wherein the food product comprises carbohydrates, proteins, and fats, wherein at least 20% by weight of the food product comprises the fats, and wherein at least 20% by weight of the fats are capric acid (C10), myristic acid (C14), or a combination of the capric acid (C10) and the myristic acid (C14).

In particular embodiments, provided herein are compositions or food products comprising carbohydrates, proteins, and fats, wherein at least 30% by weight of the food product comprises the fats, and wherein at least 35% by weight of the fats are capric acid (C10), myristic acid (C14), or a combination of the capric acid (C10) and the myristic acid (C14), for use as a medicament, and for use in the treatment of a fibrotic disease (e.g., characterized in that the food product is self-administrated). The food products, as disclosed in this application, can also be a medicament, and in particular a composition or substance for medical use as described in the application for the food product.

In certain embodiments, the capric acid (C10) and/or the myristic acid (C14) are provided in a form selected from the group consisting of: free fatty acids, esters, monoglycerides, diglycerides, triglycerides, glycolipids, and phospholipids. In further embodiments, at least 22% by weight of the food product (e.g., at least 22% . . . 45% . . . 55% . . . 65% . . . 75% . . . or 85% by weight) comprises the fats. In further embodiments, at least 27% by weight of the fats (e.g., at least 27% . . . 38% . . . 49% . . . 60% . . . 80% . . . or 95%) are the capric acid (C10), the myristic acid (C14), or the combination of the capric acid (C10) and the myristic acid (C14). In certain embodiments, 45-80% by weight of the food product is fats, and/or 25-60% by weight of the fats is capric acid (C10), myristic acid (C14), or a combination thereof. In certain embodiments, at least 75% by weight of the fats are the capric acid (C10), the myristic acid (C14), or the combination of capric acid (C10) and the myristic acid (C14).

In some embodiments, at least 10% by weight of the food product comprises the proteins (e.g., at least 10% . . . 20% . . . 30% . . . 40% . . . or 55%). In particular embodiments, at 15-30% by weight of the food product comprises the proteins. In further embodiments, at least 2% by weight of the food product comprises the carbohydrates (e.g., 2% . . . 5% . . . 10% . . . 15% . . . or 25%). In other embodiments, less than 15% by weight of the food product comprises the carbohydrates (e.g., between 1-10%, or less than 14% . . . 12% . . . 10% . . . 8% . . . 5% . . . or less than 3%). In further embodiments, less than 50% by weight of the fats are fatty acids other than the capric acid (C10), the myristic acid (C14), or the combination of capric acid (C10) and the myristic acid (C14) (e.g., less than 48% . . . 38% . . . 28% . . . 18% . . . . 10% . . . or 5%).

In certain embodiments, the food product is in a form selected from the group consisting of: mayonnaise, margarine, low fat spread, yoghurt, a fruit smoothie, a protein smoothie, a cheese spread, processed cheese, a dairy dessert, a flavored milk, cream, a fermented milk product, cheese, butter, a condensed milk product, an ice cream mix, a soy product, pasteurized liquid egg product, a bakery product, a confectionary product, confectionary bar, chocolate bar, high fat bar, energy bar, liquid emulsion, powder, spray dried powder, freeze dried powder, pudding, a gel, a gel concentrate, a liquid drink, and jelly. In some embodiments, the article of manufacture further comprises a packaging component, wherein the food product is located inside the packaging component, and wherein the food product is sealed inside the packaging component in a sterile manner. In certain embodiments, the packaging component is selected from: a foil wrapper, a plastic wrapper, a paper wrapper, a cardboard wrapper or box, a plastic or metal tub, a juice box container, a gel container, etc.

In particular embodiments, the food product is detectably free of at least one of the following: milk, eggs, peanuts, tree nuts, soy, wheat, fish, shellfish, and sulfites. In other embodiments, the food product provides 90-500 Calories (e.g., the food product within a single wrapper contains between 100 and 300 calories). In other embodiments, the food product comprises at least 10 grams (e.g., at least 11 . . . 14 . . . 18 . . . 22 . . . 25 . . . 30 . . . or 50 grams) of: the capric acid (C10), the myristic acid (C14), or the combination of the capric acid (C10) and the myristic acid (C14).

In certain embodiments, when a combination of capric acid (C10) and the myristic acid (C14) is employed, the ratio of C10 to C14 is, or is about: 5:95 . . . 10:90 . . . 20:80 . . . 30:70 . . . 40:60 . . . 50:50 . . . 60:40 . . . 70:30 . . . 80:20 . . . 90:10 . . . 95:5. In some embodiments, food product further comprises a flavoring agent.

In certain embodiments, provided herein are methods comprising: providing (e.g., shipping, dispensing at a facility, handing to the subject) the compositions or articles of manufactures described above, and herein, to a subject (e.g., human subject; male subject; or female subject) with fibrotic disease (e.g., with asthma) or a subject on a daily or alternate day Calorie restriction diet (e.g., where the subject is consuming less than 600 Calories per day). In certain embodiments, the facility is a pharmacy, hospital, or medical clinic. In certain embodiments, the providing is selected from shipping the article of manufacture to the residence of the subject, or dispensing the article of manufacture to the subject at a healthcare facility.

In some embodiments, provided herein are methods comprising: a) receiving an order for the compositions or article of manufactures described above and herein from a subject with fibrotic disease (and/or a subject on a daily or alternate day Calorie restriction diet, such as where the subject is consuming less than 600 . . . 500 . . . or 400 Calories per day), or from a caregiver of the subject with fibrotic disease; and b) shipping the article of manufacture to the subject and/or the care-giver. In certain embodiments, the methods further comprise a step of: i) receiving a prescription for the composition or article of manufacture authorizing the subject and/or the caregiver to receive the article of manufacture, or ii) verifying prescription information previously received that authorizes the subject and/or the caregiver to receive the article of manufacture (e.g., a computer or person looks a prescription already on file to ensure that the composition or article of manufacture can be sent to the subject or subject's caregiver). In further embodiments, the prescription is authorized by a healthcare provider. In further embodiments, the healthcare provider is a nurse practitioner or a physician.

In some embodiments, the fibrotic disease is selected from the group consisting of: asthma, Pulmonary fibrosis, Cystic fibrosis, Idiopathic pulmonary fibrosis, radiation-induced lung injury, Cirrhosis, Biliary atresia, Atrial Fibrosis, Endomyocardial fibrosis, Old myocardial infarction, glial scar, Arterial stiffness, Arthrofibrosis, Crohn's Disease, Dupuytren's contracture, Keloid fibrosis, Mediastinal fibrosis, Myelofibrosis, Peyronie's disease, Nephrogenic systemic fibrosis, Progressive massive fibrosis, Retroperitoneal fibrosis, and systemic sclerosis.

In certain embodiments, the prescription lists at least one, at least two, at least three, or all of the following: i) the subject's name, ii) the generic or brand name of the composition or article of manufacture, iii) the name of a healthcare provider authorizing the prescription, and iv) the amount of the composition or article of manufacture. In some embodiments, the shipping is to the subject's residence. In other embodiments, the shipping is to the caregiver's place of business. In additional embodiments, the shipping is via the U.S. Postal Service, Federal Express, United Parcel Service (UPS), or DHL. In particular embodiments, the shipping comprises providing the product to a Carrier, wherein the Carrier then delivers the article of manufacture to the subject's residence or the caregiver's place of business. In particular embodiments, the Carrier is a common carrier, a public carrier, or a private carrier.

In certain embodiments, the food product qualifies as a medical food as defined in the Orphan Drug Act. In further embodiments, the receiving the order for the composition or article of manufacture comprises receiving a request for an amount of the article of manufacture via telephone, fax, email, or paper form. In other embodiments, the receiving the order further comprises receiving payment for part or all of the composition or article of manufacture.

In some embodiments, provided herein are methods of increasing ketogenesis, decreasing appetite, suppressing appetite, or decreasing food or caloric intake, or reducing inflammation, comprising: providing an effective amount of the compositions or articles of manufacture described above, and herein, to a subject (e.g., a subject in need of such a composition or an article of manufacture to decrease appetite, suppress appetite, decrease food or calorie intake, and/or to reduce inflammation). In certain embodiments, the subject is obese, is on a weight loss diet, or has an inflammatory condition or disease. In some embodiments, the providing is selected from shipping the composition or article of manufacture to the residence of the subject, or dispensing the composition or article of manufacture to the subject at a healthcare facility. In certain embodiments, the subject receives (or consumes) no more than a total of 600 Calories (e.g., 600 . . . 550 . . . 500 . . . 450 . . . 400 . . . 350 . . . 300) per day, or every other day, from all food sources.

In particular embodiments, provided herein are methods comprising: a) administering or providing a composition or food product to a subject with fibrotic disease such that the subject receives, in a single day, at least 10 grams of capric acid (C10), myristic acid (C14), or a combination of the capric acid (C10) and the myristic acid (C14); and b) repeating the administering and/or the providing on at least two subsequent days (e.g., at least two consecutive days, or at least two days with a day in between each day that the subject receives the composition or food product). In certain embodiments, the at least 10 grams is at least 15 grams in the single day (e.g., at least 15 . . . 50 . . . 100 . . . 200 . . . 300 or 400 grams). In certain embodiments, the subject receives (or consumes) no more than a total of 600 Calories (e.g. 600 . . . 550 . . . 500 . . . 450 . . . 400 . . . 350 . . . 300) per day from all food sources.

In some embodiments, the composition comprises a food product as described above and herein. In certain embodiments, the composition is administered intravenously. In further embodiments, the composition is in the form of a pill, liquid, a capsule, gel capsule, soft gel capsule, or a syrup. In further embodiments, at least 25% by weight of the composition comprises fat (e.g., at least 30% . . . 40% . . . 65% . . . 85%), and wherein at least 35% (e.g., 35% . . . 48% . . . 65% . . . 90%) of the fat by weight comprises the capric acid (C10), the myristic acid (C14), or the combination of the capric acid (C10) and the myristic acid (C14). In certain embodiments, wherein at least 85% by weight of the composition comprises fat, and wherein at least 35% of the fat by weight comprises the capric acid (C10), the myristic acid (C14), or the combination of the capric acid (C10) and the myristic acid (C14). In further embodiments, at least 45% by weight of the composition comprises fat, and wherein at least 95% of the fat by weight comprises the capric acid (C10), the myristic acid (C14), or the combination of the capric acid (C10) and the myristic acid (C14). In further embodiments, at least 85% by weight of the composition comprises fat, and wherein at least 95% of the fat by weight comprises the capric acid (C10), the myristic acid (C14), or the combination of the capric acid (C10) and the myristic acid (C14). In further embodiments, the providing is selected from shipping the article of manufacture to the residence of the subject, or dispensing the article of manufacture to the subject at a healthcare facility. In some embodiments, the subject has asthma. In additional embodiments, the fibrotic disease is selected from the group consisting of: Pulmonary fibrosis, Cystic fibrosis, Idiopathic pulmonary fibrosis, Radiation-induced lung injury, Cirrhosis, Biliary atresia, Atrial Fibrosis, Endomyocardial fibrosis, Old myocardial infarction, glial scar, Arterial stiffness, Arthrofibrosis, Crohn's Disease, Dupuytren's contracture, Keloid fibrosis, Mediastinal fibrosis, Myelofibrosis, Peyronie's disease, Nephrogenic systemic fibrosis, Progressive massive fibrosis, Retroperitoneal fibrosis, and systemic sclerosis.

In certain embodiments, the on at least two subsequent days is on at least 14 subsequent days (e.g., at least 14 . . . 20 . . . 25 . . . 30 . . . or 50 days). In further embodiments, the on at least two subsequent days is on at least 45 subsequent days (e.g., at least 45 days . . . 8 weeks . . . 16 weeks . . . or 6 months). In further embodiments, at least 45% by weight of the composition comprises fat, wherein at least 35% of the fat by weight comprises the capric acid (C10), the myristic acid (C14), or the combination of the capric acid (C10) and the myristic acid (C14), and wherein less than 25% by weight of the fats are fatty acids other than the capric acid (C10), the myristic acid (C14), or the capric acid (C10) and the myristic acid (C14). In further embodiments, at least 45% by weight of the composition comprises fat, wherein at least 35% of the fat by weight comprises the capric acid (C10), the myristic acid (C14), or the combination of the capric acid (C10) and the myristic acid (C14), and wherein less than 15% by weight of the fats are fatty acids other than the capric acid (C10), the myristic acid (C14), or the capric acid (C10) and the myristic acid (C14).

DEFINITIONS

Figure 1:
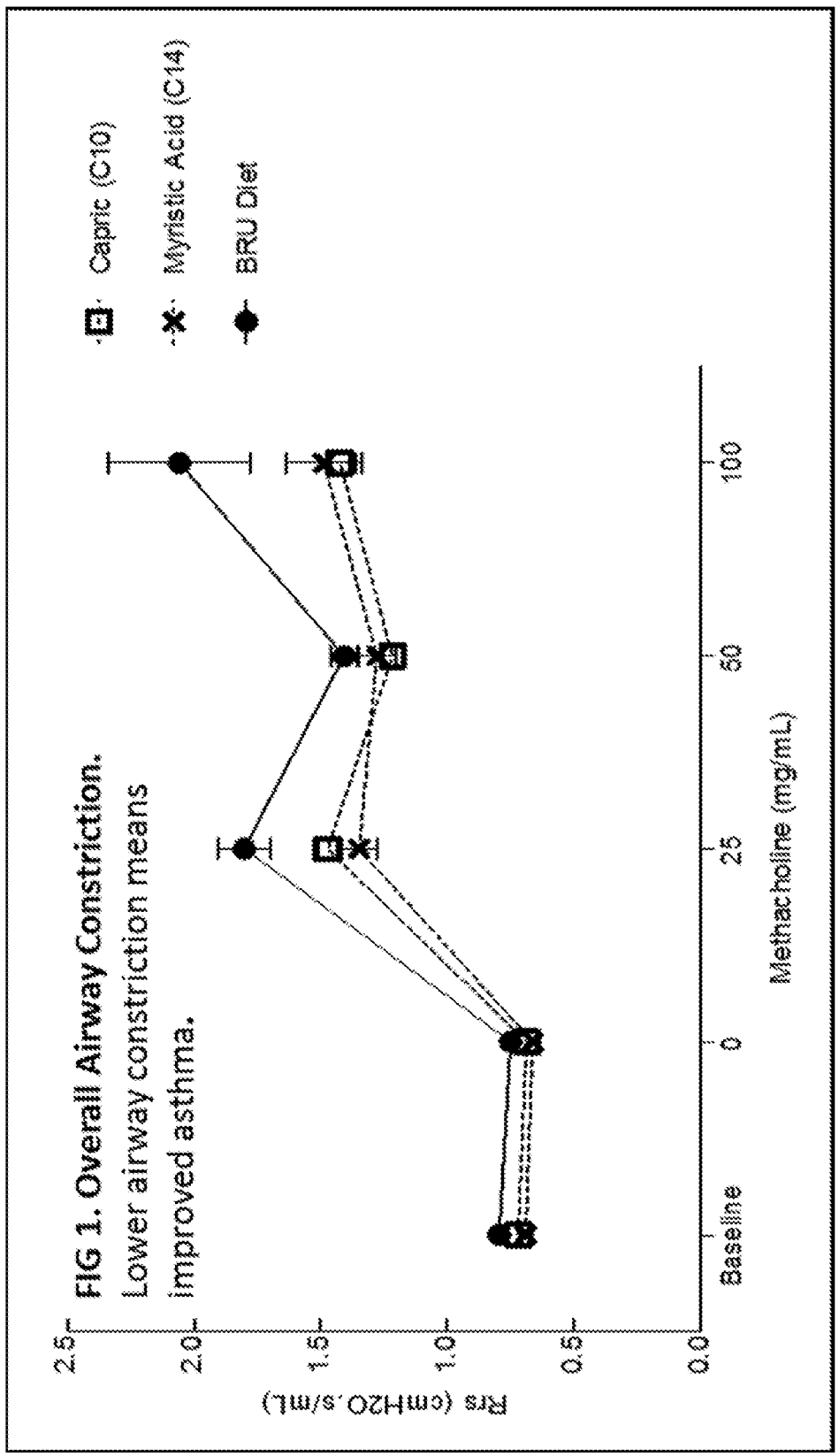
FIG. 1 shows the effects of standard diet C10 and C14 on overall airway constriction.

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. In addition, throughout the specification, the meaning of "a", "an", and "the" include plural references. The meaning of "in" includes "in" and "on."

The term "medical food," as used herein, is as defined by the Orphan Drug Act (21 U.S.C. 360ee(b)(3)) of 1988, which is "a food which is formulated to be consumed or administered enterally under the supervision of a physician and which is intended for the specific dietary management of a disease or condition for which distinctive nutritional requirements, based on recognized scientific principles, are established by medical evaluation."

As used herein, the terms "subject" and "patient" refer to any animal, such as a mammal like a dog, cat, bird, livestock, and preferably a human (e.g., a human with a disease such as asthma, a fibrotic disease, obesity, etc.).

As used herein, the term "administration" refers to the act of giving a drug, prodrug, or other agent (e.g., food product), or therapeutic treatment to a subject. Exemplary routes of administration to the human body can be through the mouth (oral), skin (transdermal, topical), nose (nasal), lungs (inhalant), oral mucosa (buccal), by injection (e.g., intravenously, subcutaneously, intratumorally, intraperitoneally, etc.), and the like.

DETAILED DESCRIPTION

Provided herein are compositions, articles of manufacture, food products, and methods for treating certain conditions, such as fibrotic disease (e.g., asthma). For example, in certain embodiments, provided herein are food products (e.g., that are ketogenic) that contain high levels (e.g., at least 10% by weight of the food product) of capric acid (C10), myristic acid (C14), or combination thereof (e.g., as free fatty acids or as triglycerides). In other embodiments, methods are provided for receiving an order for such a food product, and shipping the food product to a subject with fibrotic disease (e.g., after receiving or verifying prescription information). In some embodiments, methods are provided of administering or providing a composition to a subject such that the subject receives at least 40 grams or at least 50 per day (e.g., 200 grams per day), on multiple days, of capric acid (C10), myristic acid (C14), or combination thereof.

In certain embodiments, the food products described herein are formulated as a smoothie or similar edible food product. In certain embodiments, the food products described herein (e.g., smoothie, or bar) are accompanied by caloric restriction (e.g., to treat asthma).

In certain embodiments, a protocol is employed to explore the effects of calorie restriction on asthma health, and metabolic parameters of mitochondria UCP-2 expression and ROS generation in relation to asthma. This protocol calls for alternate-day calorie restriction to 5.5 kcal/kg (~400 kcal/day for a 70 kg individual) and will provide a formula for subjects to consume (e.g., the food products described herein) on their restriction days to enhance compliance. Because of the high level of dietary regulation of UCP-2 expression, the selection of this formula may have a significant impact on outcomes. In an animal-model study, Sullivan at al demonstrated that a ketogenic diet increases UCP-2 expression resulting in a decrease in ROS expression (Sullivan et al., Ann Neurol. 2004 April; 55(4):576-80). Since, in some embodiments, the subjects will already be restricting intake, selecting a formula to encourage ketosis will likely enhance UCP-2 expression.

The traditional formula used for inducing ketosis in ketogenic diet treatment of epilepsy is KetoCal. But this formula would only provide 8 grams of protein per 400 kcals (or 0.11 g/kg). This level of protein would likely lead to negative nitrogen balance which is not desired. Alternatively, it has been shown that ketosis in humans can be initiated in a less restricted diet with a significant portion of calories coming from medium-chain triglycerides (Liu, Epilepsia. 2008 November; 49 Suppl 8:33-6, which is herein incorporated by reference in its entirety). It has also been demonstrated in humans that higher fat diets correlate to increased expression of UCPs 2 and 3 (Schrauwen, et al., Int. J. Obes. Relat. Metab. Disord. 2001 April; 25(4):449-56). Therefore, in some embodiments, an exemplary formula has been developed to provide optimal protein levels while limiting carbohydrates and maximizing medium-chain triglycerides and total fat content in order to encourage UCP expression and support study outcomes.

The role of UCP-1 in the brown adipose tissue of rodents is well known to play a role in thermoregulation by dissipating the proton motive force as thermal energy. Because of the similar mechanism of action of UCP-2 in human adipose, it is expected that increased expression of UCP2 will lead to an increase in body temperature. Therefore, it is recommended, in some embodiments, that subjects' body temperature as well as urinary ketone levels (which will determine if the formula successfully induces ketosis) be measured periodically to examine both diet efficacy and compliance. A third measure of dietary compliance is the respiratory exchange ratio. This measure can be compared to the predicted respiratory exchange ratio (or food quotient) from the formula to test for non-compliance.

An exemplary recipe for a food product (smoothie) is as shown in Table 1 below:

TABLE 1

| Ingredient | Amount (grams) |
| --- | --- |
| Coconut milk | 395.67 |
| Yogurt, plain, whole milk* | 450.2 |

TABLE 1-continued

| Ingredient | Amount (grams) |
| --- | --- |
| Strawberries, frozen | 122.13 |
| Mango, frozen | 48.57 |
| BeneProtein** | 80.3 |
| Papaya, fresh | 54.46 |
| Vanilla extract, imitation | 7.25 |
| Ascorbic acid, crystals | 1.12 |
| Splenda | 14.0 |

*The yogurt used in the taste panel was a mixture (approx. 50/50) of plain low-fat and vanilla low-fat. The analyses included in this document use plain, whole milk as in the above recipe.
**Nestle's brand whey protein powder.

In certain embodiments, the invention addresses the potential corollary between calorie restriction on asthma health, and metabolic parameters of mitochondria UCP-2 expression and ROS generation in relation to asthma. Both the smoothie and the frozen smoothie were significantly ($P<0.05$) better than the Atkins shake in the qualities of taste, texture, and mouthfeel using a student's T-Test, and the frozen smoothie also has significantly better aftertaste.

A nutritional approach to treat asthma to help patients breathe better is provided herein. In certain embodiments, a proprietary formula is provided which is based on a ketogenic diet which includes medium chain triglyceride (MCTs) formulation (e.g., C10 and C14 fatty acids). Evidence suggests that altered cellular metabolism plays a role in asthma, and that obesity and asthma are derived from common pathway(s) that promote inflammation and adiposity. A proprietary formula for a shake/smoothie or other food product as described herein (e.g., as an alternate-day calorie restriction) is provided herein to increases UCP-expression which results in a decrease in reactive oxygen species (ROS) expression which has a profound effect on asthma health. Mitochondrial function is central in regulating metabolism and susceptibility to allergic and immunologic diseases. In the mechanism and function of mitochondria, ATP is generated via cellular respiration through the electron transport chain. In this process some reactive oxygen species (ROS) are formed which are crucial in immune signal transduction and in pathological inflammation In certain embodiments, provided herein are food products (as described herein) that provide certain generally optimum protein levels while limiting carbohydrates, maximizing medium chain triglycerides (MCTs) (e.g., that provide C10 and C14 fatty acids) and total fat content. While the present invention is not limited to any particular mechanism, and an understanding of the mechanism is not necessary to practice the invention, is it believed that such food product encourage mitochondrial uncoupling protein 2 (UCP expression-2) which in-turn attenuates mitochondrial ROS production that could alleviate symptoms of asthma (e.g., determination of inflammation by noninvasive biomarker such as urinary bromotyrosine and exhaled NO).

In some embodiments, the C10 and C14 fatty acids in the food product and compositions are esterified to a triglyceride, diglyceride, monoglyceride or phospholipid molecule. In some embodiments, the C10 and/or C14 fatty acids in the food product and compositions are provided as ethyl esters. In some embodiments, the capric acid (C10), myristic acid (C14), or combination thereof are provided in an oral delivery vehicle, food product, nutritional supplement, dietary supplement or functional food. In some embodiments, the administration of the capric acid (C10), myristic acid (C14), or combination thereof is oral, topical, parenteral, enteral, transdermal, intradermal, intraocular, intravitreal, sublingual, or intravaginal and may preferably comprise an effective amount of the composition.

In certain embodiments, the capric acid (C10), myristic acid (C14) (or combination thereof) compositions according to the present technology comprises or consists of a pharmaceutically acceptable carrier, diluent, or excipient (including combinations thereof). Acceptable carriers or diluents for therapeutic use are well known in the pharmaceutical art and are described, for example, in Remington's Pharmaceutical Sciences, Mack Publishing Co. (A. R. Gennaro edit. 1985). The choice of pharmaceutical carrier, excipient, or diluent is selected with regard to the intended route of administration and standard pharmaceutical practice. The pharmaceutical comprise as, or in addition to, the carrier, excipient, or diluent any suitable binder(s), lubricant(s), suspending agent(s), coating agent(s), and/or solubilizing agent(s). This pharmaceutical composition will desirably be provided in a sterile form. It may be provided in unit dosage form and will generally be provided in a sealed container. A plurality of unit dosage forms may be provided.

Pharmaceutical compositions within the scope of the present technology may include one or more of the following: preserving agents, solubilizing agents, stabilizing agents, wetting agents, emulsifiers, sweeteners, colorants, flavoring agents, odorants, and/or salts. Compounds of the present technology may themselves be provided in the form of a pharmaceutically acceptable salt. In addition, embodiments may comprise buffers, coating agents, antioxidants, suspending agents, adjuvants, excipients, and/or diluents. Examples of preservatives include sodium benzoate, sorbic acid, and esters of p-hydroxybenzoic acid.

They may also contain other therapeutically active agents in addition to compounds of the present technology. Where two or more therapeutic agents are used they may be administered separately (e.g., at different times and/or via different routes) and therefore do not always need to be present in a single composition. Thus, combination therapy is within the scope of the present technology.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, via the penis, vaginal, epidural, sublingual. It is to be understood that not all of the agent need be administered by the same route. Likewise, if the composition comprises more than one active component, then those components may be administered by different routes.

If the C10 and/or C14 agent of the present technology is administered parenterally, then examples of such administration include one or more of: intravenously, intra-arterially, intraperitoneally, intrathecally, intraventricularly, intraurethrally, intrastemally, intracranially, intramuscularly, or subcutaneously administering the agent; and/or by using infusion techniques.

In some embodiments, pharmaceutical compositions adapted for oral administration are provided as capsules or tablets; as powders or granules; as solutions, syrups or suspensions (in aqueous or non-aqueous liquids); as edible foams or whips; or as emulsions. Tablets or hard gelatin capsules may comprise lactose, maize starch or derivatives thereof, stearic acid or salts thereof. Soft gelatin capsules may comprise vegetable oils, waxes, fats, semi-solid, or liquid polyols etc. Solutions and syrups may comprise water, polyols and sugars. For the preparation of suspensions, oils (e.g., vegetable oils) may be used to provide oil-in-water or water-in-oil suspensions. An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Alternatively, the C10 and/or C14 agent of the present technology may be applied topically in the form of a gel, hydrogel, lotion, solution, cream, ointment or dusting powder. The agent of the present technology may also be dermally or transdermally administered, for example, by the use of a skin patch. For application topically to the skin, the agent of the present technology can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. If the agent of the present technology is administered parenterally, then examples of such administration include one or more of: intravenously, intra-arterially, intraperitoneally, intrathecally, intraventricularly, intraurethrally, intrastemally, intracranially, intramuscularly or subcutaneously administering the agent; and/or by using infusion techniques.

For parenteral administration, the agent is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Typically, a physician will determine the actual dosage which will be most suitable for an individual subject. The specific dose level and frequency of dosage for any particular patient may be varied and will depend upon a variety of factors including the activity of the specific compound employed; the metabolic stability and length of action of that compound; the age, body weight, general health, sex, diet, mode and time of administration; rate of excretion; drug combination; the severity of the particular condition; and the individual undergoing therapy. The agent and/or the pharmaceutical composition of the present technology may be administered in accordance with a regimen of from 1 to 10 times per day, such as once or twice per day. For oral and parenteral administration to human patients, the daily dosage level of the agent may be in single or divided doses.

Depending upon the need, the agent may be administered at a dose of from 1 g/kg to 10/kg body weight, per day. Naturally, the dosages mentioned herein are exemplary of the average case. There can, of course, be individual instances where higher or lower dosage ranges are merited.

"Therapeutically effective amount" refers to the amount of the therapeutic agent that is effective to achieve its intended purpose, i.e., treating symptoms of asthma or a reduction of inflammation and associated symptoms. The methods described herein may employ a daily therapeutically effective amount. While individual patient needs may vary, determination of optimal ranges for effective amounts of the compounds related to the technology is within the skill of the art. Generally, the dosage regimen for treating a condition with the compounds and/or compositions of this technology is selected in accordance with a variety of factors, including the type, age, weight, sex, diet and medical condition of the patient; the severity of the dysfunction; the route of administration; pharmacological considerations such as the activity, efficacy, pharmacokinetic and toxicology profiles of the particular compound used; whether a drug delivery system is used; and whether the compound is administered as part of a drug combination and can be adjusted by one skilled in the art. Thus, the dosage regimen actually employed may vary widely and therefore may deviate from the exemplary dosage regimens set forth herein.

EXAMPLES

Example 1

Capric Acid (C10) and Myristic Acid (C14) Improve Symptoms of Asthma

Medium chain fatty acid (MCF) composition of natural coconut oil is shown in the table below Table 1 below.

TABLE 1

| C8:0 5-9% | C16:0 8-11% |
|---|---|
| C10:0 4-10% | C18:0 8-14% |
| C12:0 44-52% | C18:1 1.5% max |
| C14:0 13-21% | C18:2 0.5% max |

Mice were fed with standard, coconut oil or MCF supplemented diets starting six weeks before allergen sensitization. Isofluorane anesthetized mice received 100 ug house dust mite (*D. pteronyssinus*) extract (HDME) (Greer Labs, NC) in 50 ug saline by nasal aspiration. Five days later mice were challenged daily with 10 ug HDME for 5 days. Three days, after the last HDME exposure, airway hyper-reactivity is measured and lungs collected for analysis. The diets were 15 kcal % fat at a dose of 21 g coconut oil or purified MCF per kg diet. Based on the daily food intake of 4.75 g/day/25 g mouse, each mouse consumes 100 mg of coconut oil or MCF per day.

TABLE 2

| MCF | Natural Coconut Oil MCF Composition | Daily Intake per mouse fed with coconut oil | Daily Intake per mouse fed with purified MCF diet |
|---|---|---|---|
| C8 | 5-9% | 5-9 mg | 100 mg (4 g/kg body weight) |
| C10 | 4-10% | 4-10 mg | 100 mg (4 g/kg body weight) |
| C12 | 44-52% | 44-52 mg | 100 mg (4 g/kg body weight) |
| C14 | 13-21% | 13-21 mg | 100 mg (4 g/kg body weight) |
| C12/C14 | — | — | 70/30 mg (2.8 g C12; 1.2 g C14/kg bodyweight) |

Figure 2:
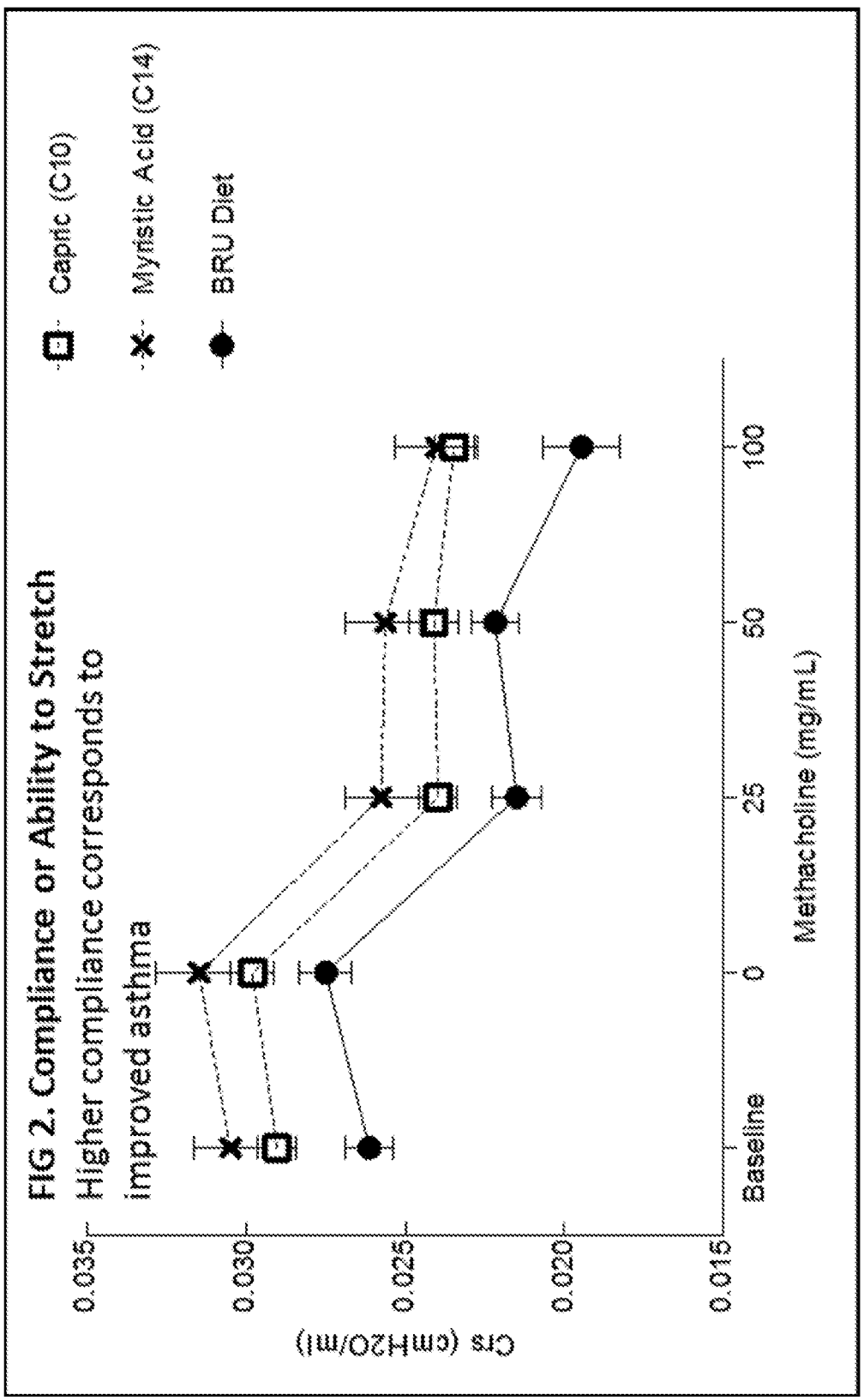
FIG. 2 shows effects of standard diet C10 and C14 on lung compliance.
Figure 3:
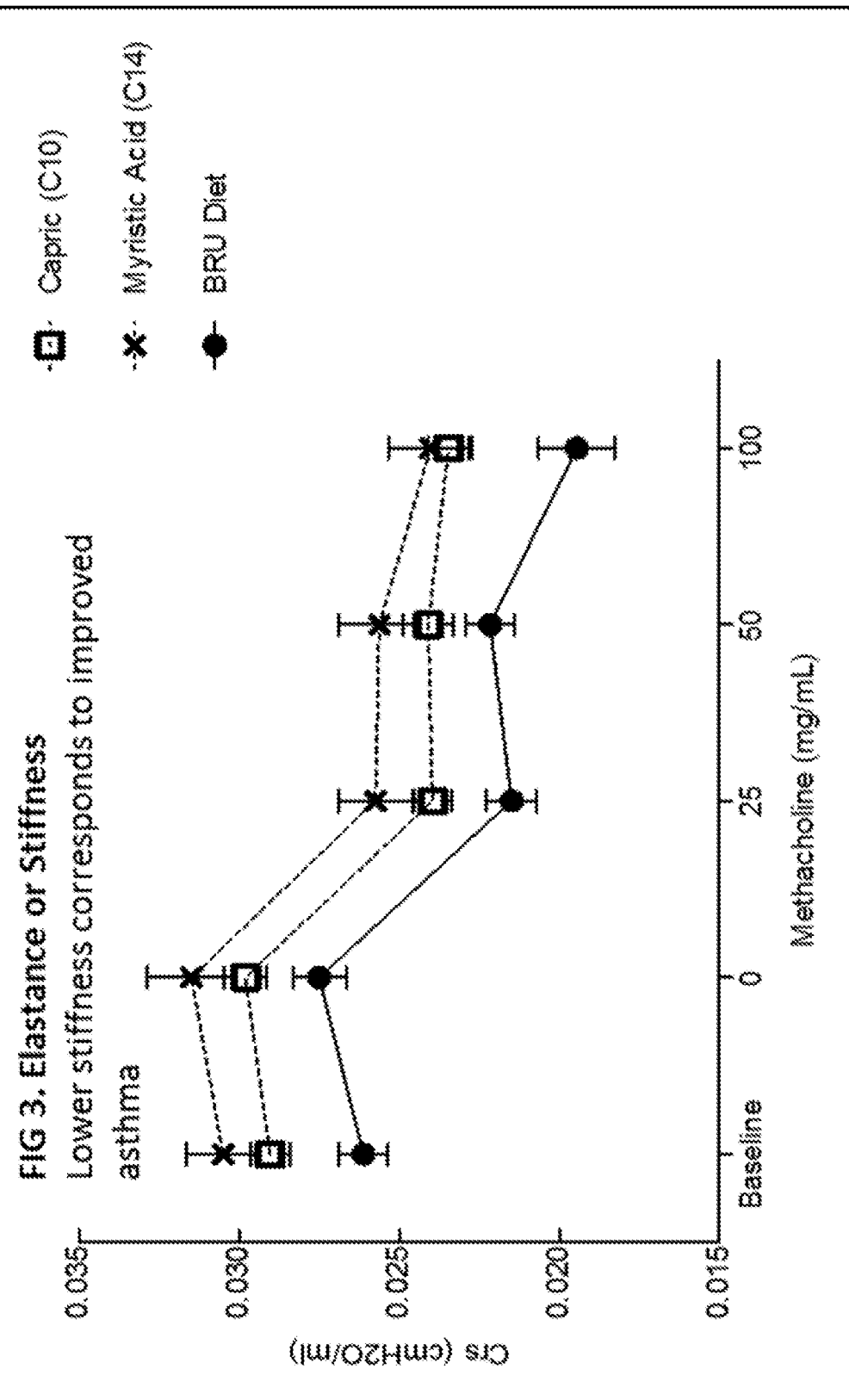
FIG. 3 shows effects of standard diet C10 and C14 on lung stiffness.
Figure 4:
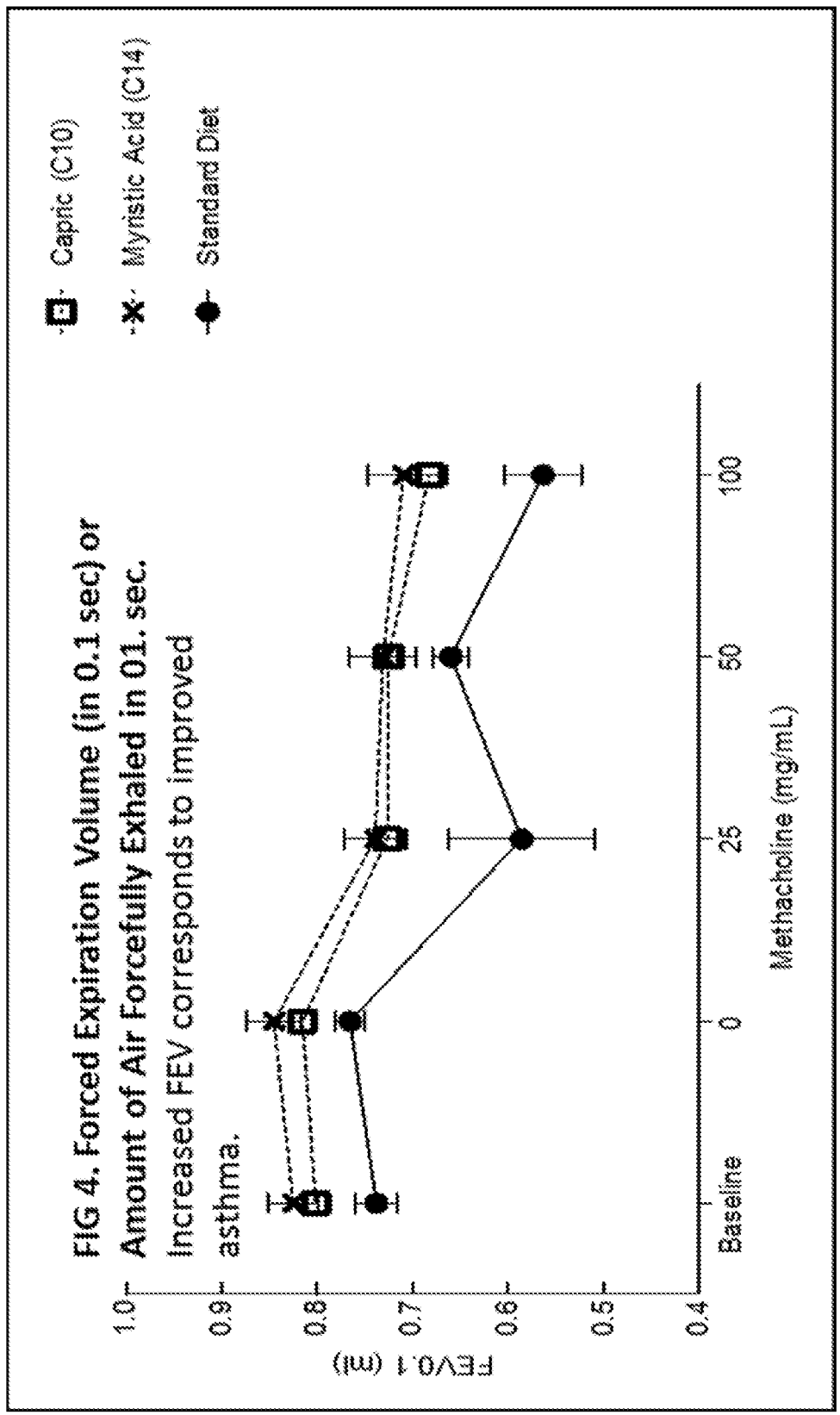
FIG. 4 shows effects of standard diet C10 and C14 on forced expiratory lung volume.

The results of this examples are shown in FIGS. 1-4, which show the results with the mice treated with the various fatty acids, which are present mainly as triglycerides in coconut oil. FIG. 1 shows that overall airway constriction (Rrs on Y-axis) induced by increasing dose of methacholine, a bronchoconstrictor, (x-axis) is inhibited in animals fed with C10 or C14. FIG. 2 shows that the ability of the lungs to stretch (Crs on Y-axis) in response to an increasing dose of methacholine (x-axis) is improved in animals fed with C10 or C14. FIG. 3 shows that stiffness the lungs (Ers on Y-axis) in response to an increasing dose of methacholine (x-axis) is decreased in animals fed with C10 or C14. FIG. 4 shows that the amount of forcefully exhaled air (FEV on Y-axis) in response to increasing dose of methacholine, (x-axis) is increased in animals fed with C10 or C14.

Example 2

Figure 5:
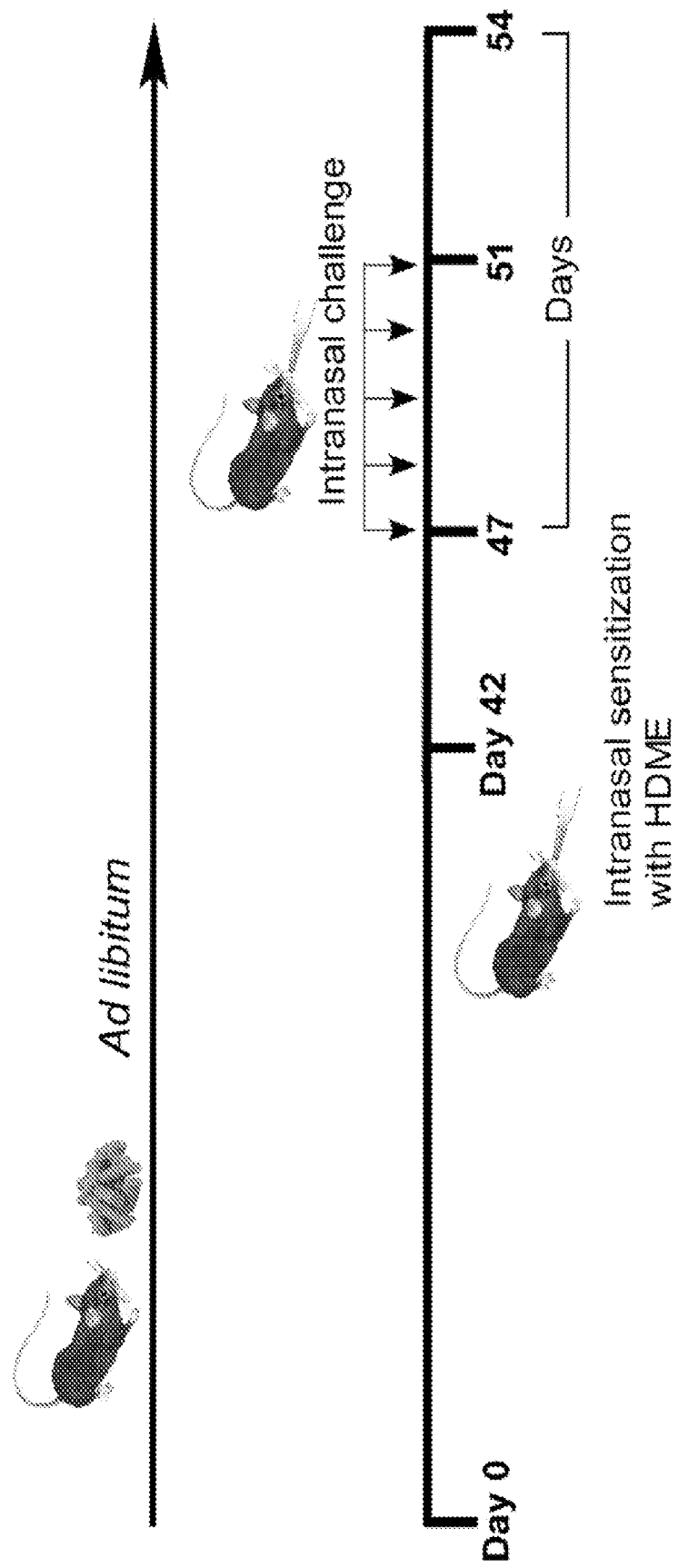
FIG. 5 shows experimental design of animals fed with various dosages of coconut oil in a mouse house dust mite model.

Effect of Coconut Diet on Airway Hyper-Reactivity in a Preclinical Mouse Model of House Dust Mite Induced Asthma Experimental Outline and Results are as follows. Mice were fed with standard or coconut oil supplemented diets starting six weeks before allergen sensitization. Isofluorane anesthetized mice received 100 ug house dust mite (*D. pteronyssinus*) extract (HDME) (Greer Labs, NC) in 50 ug saline by nasal aspiration. Five days later mice are challenged daily with 10 ug HDME for 5 days. Three days, after last HDME exposure, airway hyper-reactivity is measured and lungs collected for analysis (FIG. 5).

Figure 6A:
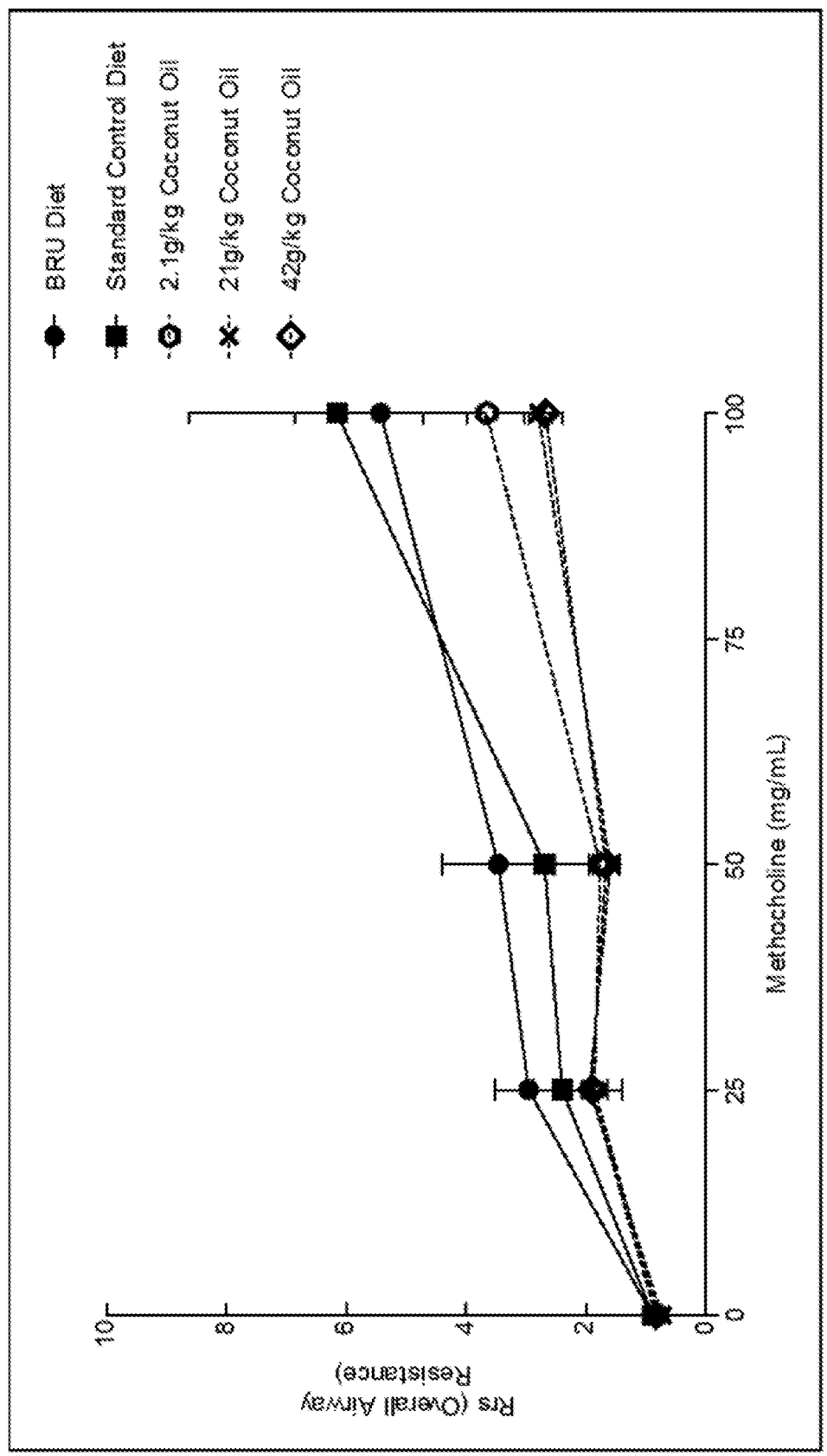
FIG. 6A shows overall airway constriction.
Figure 6B:
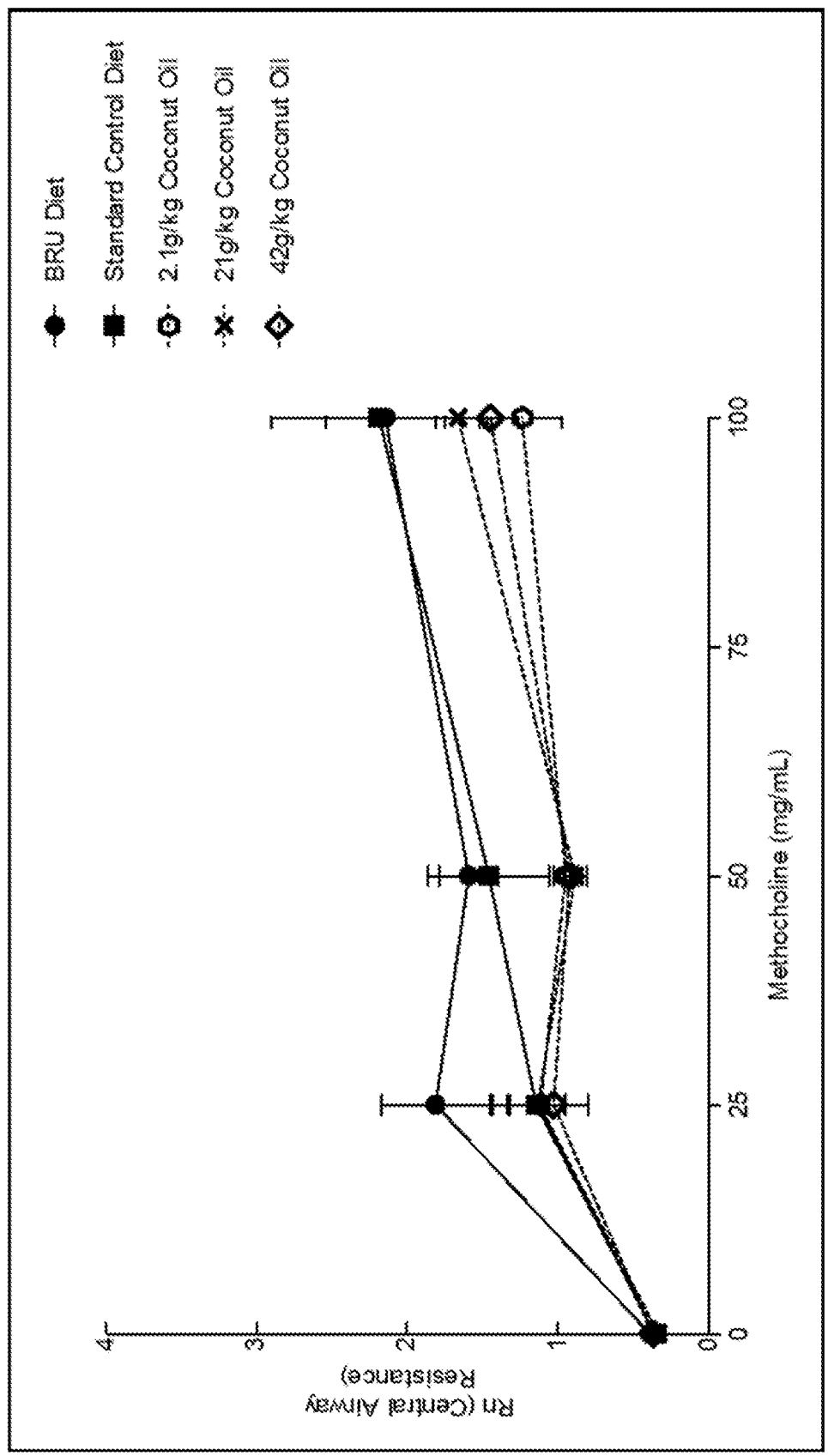
FIG. 6B shows central airway constriction.
Figure 6C:
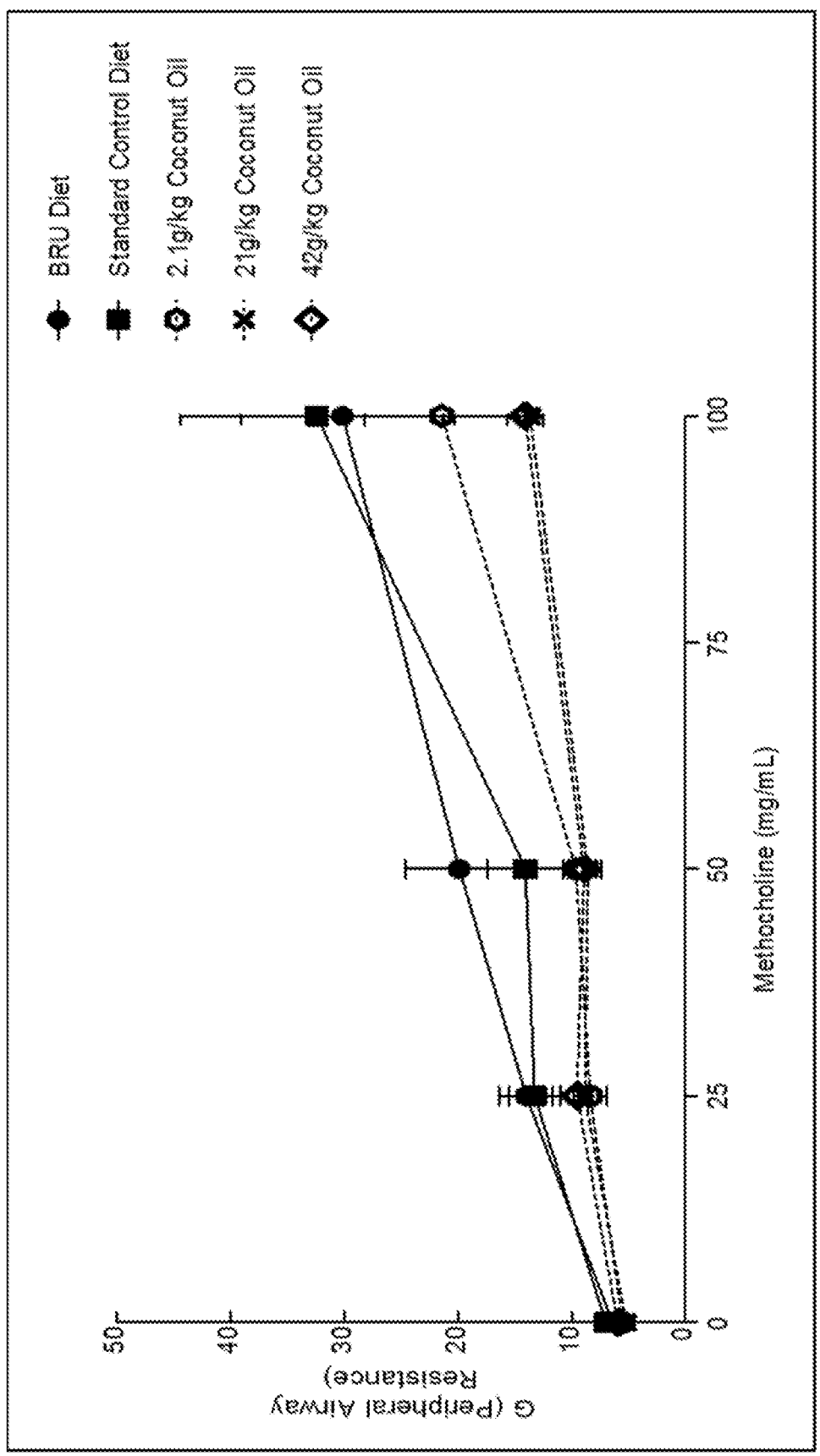
FIG. 6C shows peripheral airway constriction.
Figure 6D:
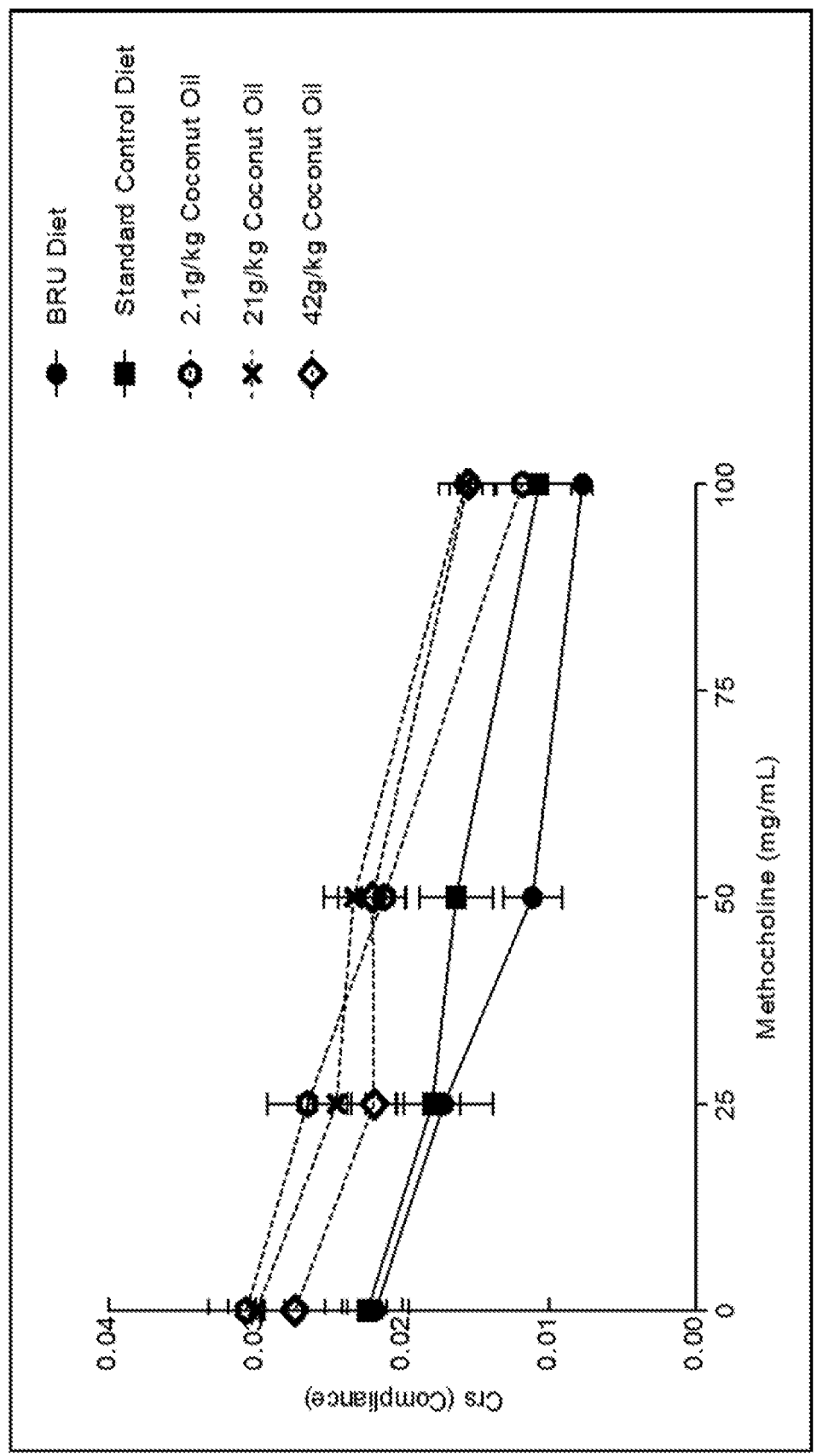
FIG. 6D shows lung compliance.
Figure 6E:
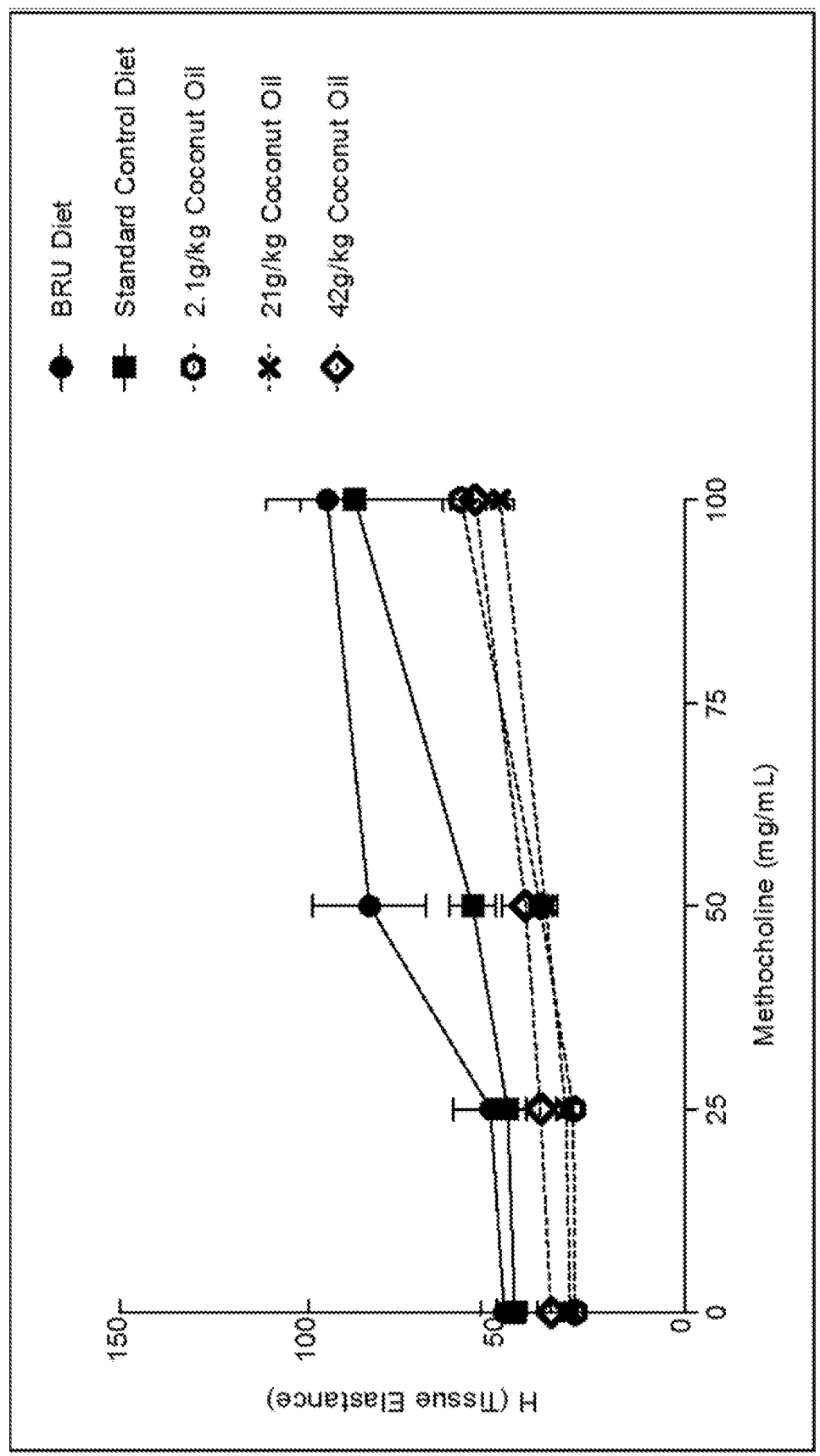
FIG. 6E shows peripheral lung tissue elastance.
Figure 6F:
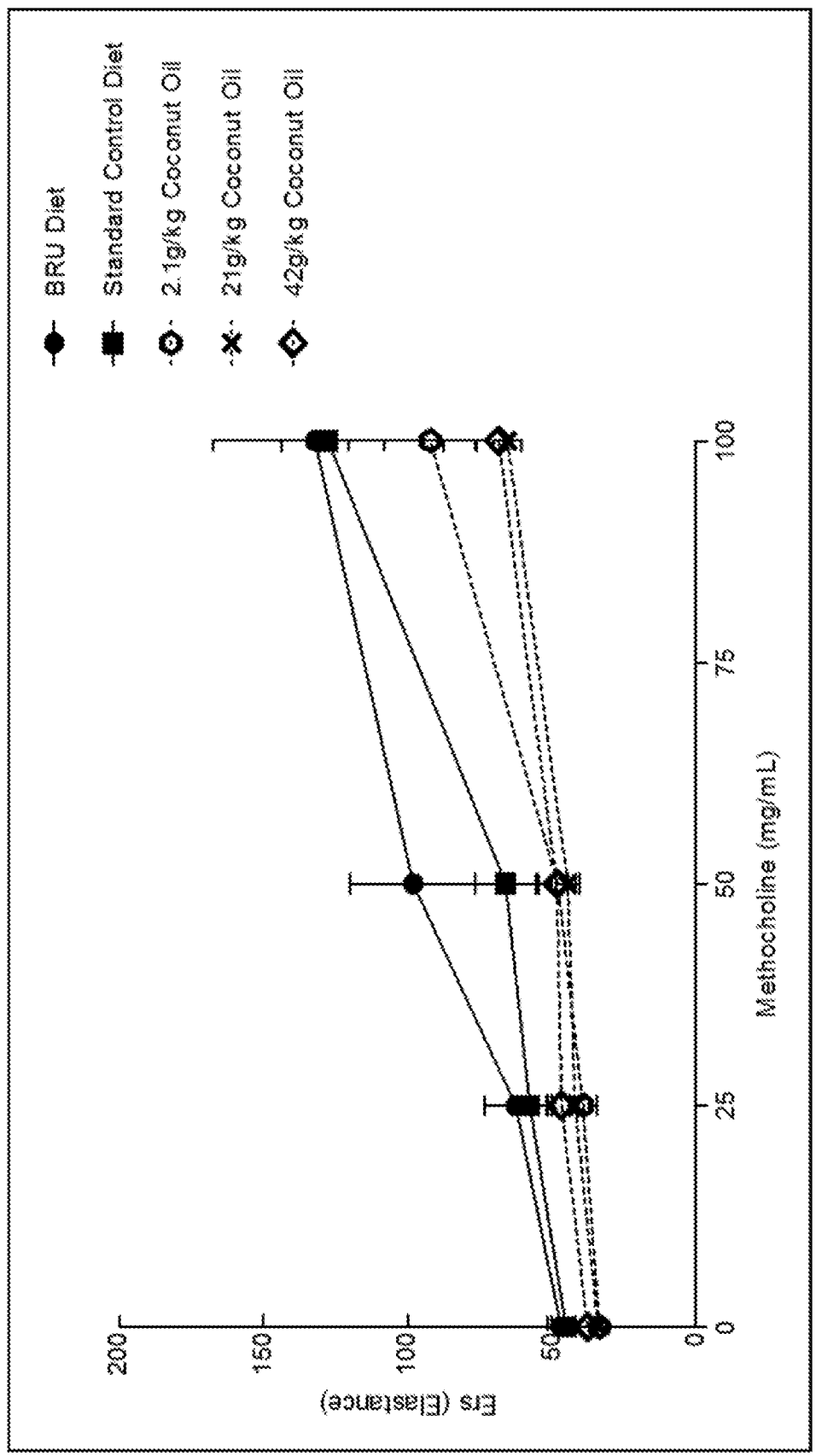
FIG. 6F shows lung elastance.

As shown in FIG. 6A-C, coconut oil diet reduced airway resistance (FIG. 6A-C) in a dose dependent manner: overall, central and peripheral airway hyper-reactivity were decreased. Lung compliance and elastance parameters showed coconut oil dose-dependent decreased of lung stiffness (FIG. 6D-F). The work shown in FIG. 6 was conducted as follows. Measurement of lung mechanics was performed using the FlexiVent ventilator (FlexiVent, Scireq, Montreal, Canada). Airway Hyperresponsiveness and lung mechanics were measured in response to increasing doses of inhaled methacholine. (A-C) Parameters of airway resistance. (D) Tissue compliance, which is inversely related to lung stiffness. (E-F) Lung elastance parameters.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

We claim:

1. A composition comprising: carbohydrates, proteins, and fats,
   wherein at least 30% by weight of the composition comprises the fats, and wherein at least 50% by weight of the fats are a combination of capric acid (C10) and myristic acid (C14), and
   wherein the ratio of C10 to C14 is: 80:20-90:10.

2. The composition of claim 1, wherein the capric acid (C10) and the myristic acid (C14) are provided in a form selected from the group consisting of: free fatty acids, esters, diglycerides, glycolipids, and phospholipids.

3. The composition of claim 1, wherein at least 60% by weight of the composition comprises the fats.

4. The composition of claim 1, wherein the capric acid (C10) and the myristic acid (C14) are in the form of triglycerides.

5. The composition of claim 1, wherein at least 10% by weight of the composition comprises the proteins.

6. The composition of claim 1, wherein less than 15% by weight of the composition comprises the carbohydrates.

7. The composition of claim 1, wherein the composition is in a form selected from the group consisting of: liquid emulsion, powder, spray dried powder, freeze dried powder, and a liquid drink.

8. The composition of claim 1, wherein the composition is detectably free of at least one of the following: eggs, peanuts, tree nuts, soy, wheat, fish, shellfish, and sulfites.

9. The composition of claim 1, wherein the composition provides 90-500 Calories.

10. The composition of claim 1, wherein the composition comprises at least 10 grams of: the combination of the capric acid (C10) and the myristic acid (C14).

11. The composition of claim 1, wherein at least 10% by weight of the composition comprises said carbohydrates.

12. An article of manufacture comprising a food product comprising: carbohydrates, proteins, and fats,
    wherein at least 65% by weight of the food product comprises the fats, and wherein at least 60% by weight of the fats are a combination of capric acid (C10) and myristic acid (C14), and
    wherein the ratio of C10 to C14 is: 80:20-90:10.

13. The article of claim 12, wherein said food product is in the form of a powder.

14. The article of claim 13, wherein said powder is a spray dried powder or a freeze dried powder.

15. The article of claim 12, wherein said food product is in the form of a liquid.

16. The article of claim 12, wherein at least 10% by weight of the food product comprises the proteins.

17. The article of claim 12, wherein the capric acid (C10) and the myristic acid (C14) are in the form of triglycerides.

18. An article of manufacture comprising a food product comprising: carbohydrates, proteins, and fats,
    wherein said foot food product is in the form of a powder,
    wherein at least 65% by weight of the food product comprises the fats, and wherein at least 60% by weight of the fats are a combination of capric acid (C10) and myristic acid (C14),
    wherein the ratio of C10 to C14 is: 80:20-90:10, and
    wherein the capric acid (C10) and the myristic acid (C14) are in the form of triglycerides.

19. The article of claim 18, further comprising a packaging component, wherein the food product is located inside the packaging component, and wherein food product is sealed inside the packaging component in a sterile manner.

* * * * *